United States Patent [19]

Johnson

[11] Patent Number: 5,653,224

[45] Date of Patent: Aug. 5, 1997

[54] NASAL DILATOR WITH AREAS OF ADHESIVE ENGAGEMENT OF VARYING STRENGTH

[75] Inventor: Bruce C. Johnson, St. Paul, Minn.

[73] Assignee: Creative Integration & Design, Inc., St. Paul, Minn.

[21] Appl. No.: 659,283

[22] Filed: Jun. 6, 1996

Related U.S. Application Data

[63] Continuation-in-part of Ser. No. 183,916, Jan. 19, 1994, Pat. No. 5,533,499, which is a continuation of Ser. No. 48,589, Apr. 16, 1993, abandoned, which is a continuation of Ser. No. 884,626, May 15, 1992, abandoned, which is a continuation of Ser. No. 712,508, Jun. 10, 1991, abandoned.

[51] Int. Cl.[6] .................... A61M 15/00; A61M 29/00; A62B 7/00; A61B 17/00

[52] U.S. Cl. .................. 128/200.24; 128/207.18; 128/848; 602/41; 602/74; 602/902; 606/199; 606/201; 606/204.45

[58] Field of Search ................. 128/200.24, 207.18, 128/912, 848, DIG. 26; 602/41, 52, 54–60, 74, 902; 606/199, 201, 204.45

[56] References Cited

U.S. PATENT DOCUMENTS

| | | | |
|---|---|---|---|
| 850,978 | 4/1907 | Soares . | |
| 1,043,924 | 11/1912 | Gottlieb | 606/199 |
| 1,292,083 | 1/1919 | Sawyer . | |
| 1,950,839 | 3/1934 | Chirila | 128/199 |
| 2,001,862 | 5/1935 | Battey . | |
| 2,398,073 | 4/1946 | Bonde | 128/87 R |
| 2,509,157 | 5/1950 | Lind | 128/87 |
| 2,566,148 | 8/1951 | Sky | 128/117 |
| 2,586,219 | 2/1952 | Geffas | 128/117 |
| 2,625,931 | 1/1953 | Phillips | 128/104 |
| 3,046,989 | 7/1962 | Hill | 128/207.18 |
| 3,426,751 | 2/1969 | Radewan | 128/76 |
| 3,531,090 | 9/1970 | Laible | 256/10 |
| 3,742,943 | 7/1973 | Malmin | 128/76 C |
| 3,835,848 | 9/1974 | Berner | 128/76 C |
| 3,935,859 | 2/1976 | Doyle | 128/89 R |
| 4,153,051 | 5/1979 | Shippert . | |
| 4,213,452 | 7/1980 | Shippert | 128/89 R |
| 4,274,402 | 6/1981 | Shippert | 128/89 R |
| 4,340,040 | 7/1982 | Straith | 128/76 C |
| 4,402,314 | 9/1983 | Goode | 128/76 C |

(List continued on next page.)

FOREIGN PATENT DOCUMENTS

| | | | |
|---|---|---|---|
| 437661 | 11/1926 | Germany | 128/76 C |
| 453006 | 3/1928 | Germany | 128/76 C |
| 12987 | 9/1990 | United Kingdom | 128/76 C |
| 9118567 | 12/1991 | WIPO | 128/842 |

OTHER PUBLICATIONS

Pp. 11 and 12 of Specification Sheet of CoNco entitled "Nasal Splint—Disposable Glove".

Copy of Packaging containing a Nasal Strip sold prior to the filing of this application by Bolinger Industries.

*Primary Examiner*—Kimberly L. Asher
*Attorney, Agent, or Firm*—Kinney & Lange, P.A.

[57] ABSTRACT

A nasal dilator that prevents the outer wall tissue of the nasal passages of the nose from drawing in during breathing comprises a truss member. The truss member includes a flexible strip of material having a first end region, a second end region and an intermediate segment. The first and second end regions are adapted to engage the outer wall tissue of first and second nasal passages of the nose. The intermediate segment is configured to traverse a portion of a nose located between the first and second nasal passages, and a pad can be provided to prevent adhesion of the intermediate segment to the nose. The truss member further includes first and second resilient bands secured to the strip of material adjacent opposite edges of the intermediate segment. The resiliency of the first and second resilient bands acts to stabilize the outer wall tissue and thereby prevents the outer wall tissue of the first and second nasal passages from drawing in during breathing. Rather than a pad preventing adhesion, an adhesion reduction can be provided by a partial adhesion arrangement.

9 Claims, 5 Drawing Sheets

U.S. PATENT DOCUMENTS

| | | | |
|---|---|---|---|
| 4,414,977 | 11/1983 | Rezakhany | 128/342 |
| 4,534,342 | 8/1985 | Paxa . | |
| 4,674,133 | 6/1987 | Oschner | 2/9 |
| 4,823,789 | 4/1989 | Beisang, III | 128/207.18 |
| 4,932,943 | 6/1990 | Nowak | 238/DIG. 26 |
| 4,971,282 | 11/1990 | Dickinson | 248/231.8 |
| 4,984,302 | 1/1991 | Lincoln | 2/206 |
| 4,995,114 | 2/1991 | Price, Jr. | 2/15 |
| 5,003,971 | 4/1991 | Buckley | 128/156 |
| 5,022,389 | 6/1991 | Brennan | 128/76 C |
| 5,101,837 | 4/1992 | Perrin | 128/888 |
| 5,209,801 | 5/1993 | Smith | 602/41 |
| 5,476,091 | 12/1995 | Johnson | 128/200.24 |
| 5,533,503 | 7/1996 | Doubek et al. | 128/207.18 |
| 5,546,929 | 8/1996 | Muchin | 128/207.18 |
| 5,553,605 | 9/1996 | Muchin | 128/207.18 |

NASAL DILATOR WITH AREAS OF ADHESIVE ENGAGEMENT OF VARYING STRENGTH

This is a continuation-in-part of application Ser. No. 08/183,916, filed Jan. 19, 1994, now U.S. Pat. No. 5,533, 499, which was a continuation of the application having Ser. No. 08/048,589, filed Apr. 16, 1993, now abandoned, which was a continuation of the application having Ser. No. 07/884,626, filed on May 15, 1992, now abandoned, which was a continuation of the application having Ser. No. 07/712,508, now abandoned, filed on Jun. 10, 1991.

BACKGROUND OF THE INVENTION

This invention relates generally to the field of devices for the treatment of malformations. In particular, the present invention is a nasal dilator for preventing outer wall tissue of nasal passages of a nose from drawing in during breathing.

A portion of the human population has some malformation of the nasal passages which makes breathing difficult. Example of such malformations are a deviated septum and swelling due to allergic reactions. The lower portion of the nostril, immediately above the entrance to the nostril, is known as a vestibule. The vestibule tapers inwardly to a narrowed neck-like area called the ostium internum. Above the ostium internum the nasal passages widen out again. Nasal obstructions commonly occur at the ostium in individuals who have swelling due to allergic reactions, a deviated septum or similar condition, to the point that the ostium may be substantially blocked. Commonly, the lateral wall (i.e., the outer wall tissue of the nasal passage) at the ostium is loose with the result that the outer wall tissue draws in during the process of inhalation to substantially block the passage of air through the nasal passage. The drawing in of the outer wall tissue act as a "check valve" to block air flow during in-breathing.

Blockage of the nasal passages is obviously an inconvenience to persons who experience it. In particular, sustained mouth breathing over a long period of time may cause lung irritation due to the inhalation of foreign particles that would otherwise be filtered if the breath had been passed through the nose. Blockage of the nasal passages is particularly uncomfortable at night, since it is difficult for a person who has such a problem to breathe through the mouth while asleep. Nasal blockage can lead to sleep disturbances and irregularities, since a person with such a condition may wake often because he/she is not inhaling sufficient quantities of oxygen.

The most common approach to a serious and chronic nasal blockage problem as described above is a surgical attempt to correct the malformation of the nasal passages. However, surgery is expensive and may not ultimately correct the problem.

As an alternative to surgery, nasal dilators for aiding breathing through the nose are generally known. U.S. Pat. No. 4,414,977 to Rezakhany discloses one such nasal dilator. The nasal dilator includes generally elongated top and bottom rings which are spaced apart and connected together by a rear strut and a front strut. The front strut is longer than the rear strut and includes a bend therein formed at a position close to the front end of the bottom ring. When in place in the nasal passage, the top ring fits in the ostium within the nostril to prevent the tissue from being drawn in during inhalation, and to reduce extra flow resistance during exhalation. The bottom ring fits above the entrance to the nostril and serves to stabilize the position of the top ring within the nasal passage. One of these nasal dilators must be inserted into each nasal passage to provide unobstructed breathing.

However, these nasal dilators are not always effective since they are uncomfortable to wear. Because the nasal dilators must be inserted within the nasal passages they may cause irritation and itching. In addition, these nasal dilators must be custom-made to fit each nasal passage of an individual.

There are also known external nasal dilators such as those in U.S. Pat. Nos. 1,292,083 to Sawyer and U.S. Pat. No. 1,950,839 to Chirila which attach to the outer wall tissues of the nasal passages to pull outwardly thereon. Such external dilators have been inconvenient and unwieldy in being formed of multiple parts requiring adjustment to operate together satisfactorily and bearing the risk of unwanted disassembly due to disturbance forces encountered during use.

It is evident that there is a continuing need for improved nasal dilators for preventing outer wall tissue of nasal passages of a nose from drawing in during breathing. Specifically, there is a need for a nasal dilator that can provide effective relief without the need of inserting an object within the nasal passage. Moreover, there is a need for a nasal dilator that can be worn at night when the nasal blockage problem is most acute and most uncomfortable and external disturbance forces are most often encountered as a result of movement head and pillow movement during hours intended for sleeping. A dilator should be of efficient design and relatively uncomplicated and provide effective stabilization of the outer wall tissue of the nasal passages to provide effective relief from nasal blockage during inhalation. In addition, the nasal dilator should provide this effective stabilization without undue discomfort or risk to the wearer.

SUMMARY OF THE INVENTION

The present invention is a nasal dilator for preventing outer wall tissue of nasal passages of a nose from drawing in during breathing. The nasal dilator comprises a tress member having a first end region adapted to engage the outer wall tissue of a first nasal passage. A second end region of the truss member is configured to engage the outer wall tissue of a second nasal passage. The first and second end regions of the truss member are coupled to one another by an intermediate segment. The intermediate segment is configured to traverse a portion of the nose located between the first and second nasal passages. The truss member, when in place, acts to stabilize the outer wall tissue and thereby prevent the outer wall tissue of the first and second nasal passages from drawing in during breathing.

The tress member includes a flexible strip of material that defines the first and second end regions and the intermediate segment of nasal dilator. A first resilient band is secured to a first side of the strip of material adjacent a first edge of the material. A second resilient band spaced from the first resilient band is secured to the first side of the strip of material adjacent a second edge thereof. The first and second resilient bands are oriented generally parallel to one another and substantially parallel to the longitudinal extent of the strip of material.

Each of the first and second resilient bands includes a plurality of grooves that extend substantially parallel to the respective resilient band. The grooves create areas of reduced material to enhance the flexibility oft he first and second resilient bands in a direction perpendicular to the grooves. In addition, each of the first and second resilient bands includes first and second angled ends. The first and second angled ends extend towards the first side of the strip of material and help to prevent the first and second resilient bands from readily separating from the strip of material when the truss member is flexed. The resiliency of the first and second resilient bands prevent the outer wall tissue of the first and second nasal passages from drawing in during breathing.

The truss member further includes an adhesive substance located on a second side of the flexible strip of material. The adhesive substance acts to releasably secure the truss member to the outer wall tissue of the first and second nasal passages, particularly the adhesive substance portions on the surfaces near the ends of the second side of the flexible strip of material in the truss member. A pad at a surface intermediate to these end surfaces can be used to prevent adhesion to the bridge of the wearer's nose for added convenience and comfort. Rather than such a pad, an arrangement can be used at this intermediate surface permitting partial adhesion to the bridge of the wearer's nose for greater comfort. First and second release liners cover the adhesive substance on the first and second end regions. The first and second release liners are readily removable from the strip of material to expose the adhesive substance and permit the tress member to be secured to the outer wall tissue of the first and second nasal passages.

This nasal dilator is of efficient design and effectively prevents the outer wall tissue of the first and second nasal passages of the nose from drawing in during breathing. In addition, the nasal dilator provides effective relief of nasal blockage during inhalation without the irritation and discomfort normally associated with nasal dilators that are inserted within the nasal passages. Moreover, this nasal dilator can be worn at night when the inhalation nasal blockage problem is most acute, without the anxiety and inconvenience normally associated with custom made, internally worn nasal dilators or multiple and separable part external dilators.

DETAILED DESCRIPTION OF THE PREFERRED EMBODIMENTS

Figure 1:
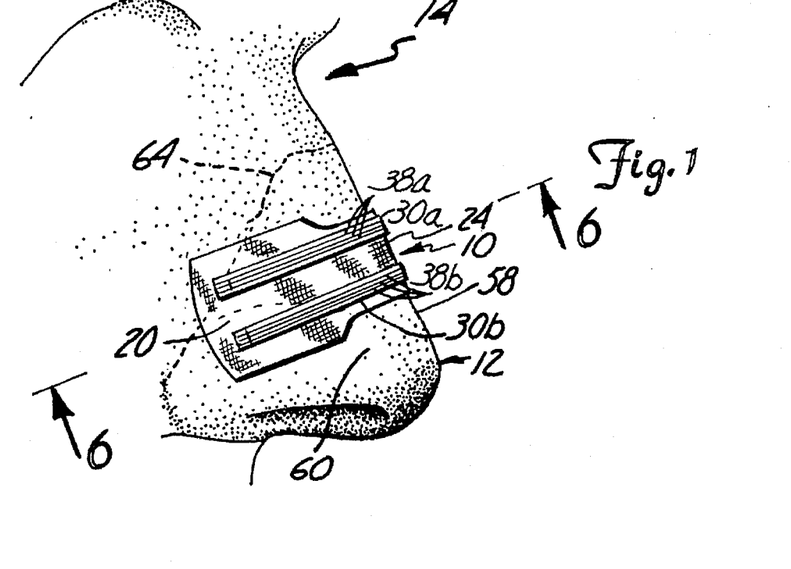
FIG. 1 is perspective view of a portion of a face with a nasal dilator in accordance with the present invention secured to a nose.

A nasal dilator 10 in accordance with the present invention is illustrated generally in FIG. 1. The nasal dilator 10 is shown secured to a nose 12 of a wearer 14.

Figure 2:
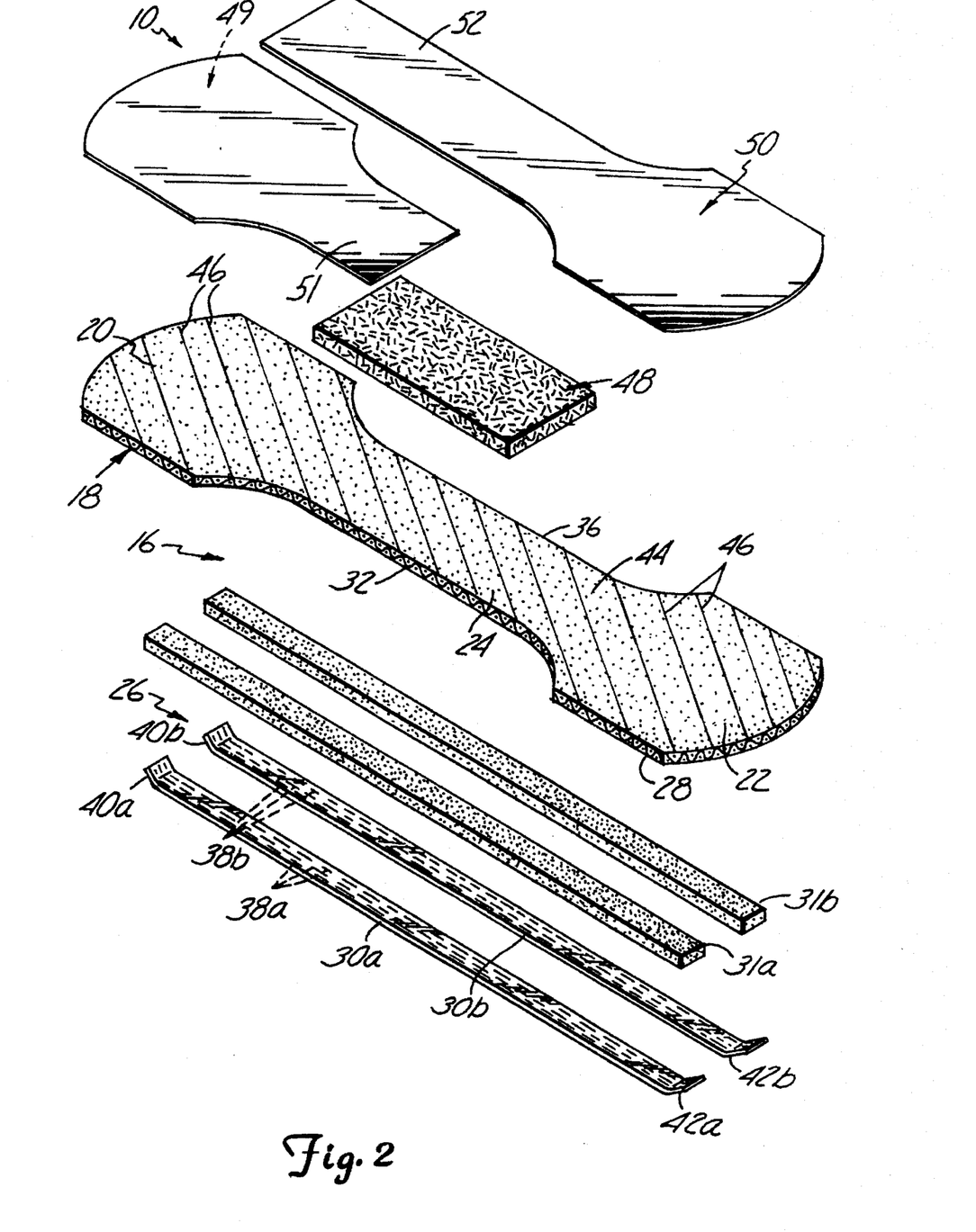
FIG. 2 is an exploded perspective view showing the components of the nasal dilator in accordance with the present invention.

As seen in FIG. 2, the nasal dilator 10 comprises a truss member 16 including a flexible strip of material 18 having a first end region 20 and a second end region 22 coupled to the first end region 20 by way of an intermediate segment 24. The width of the intermediate segment 24 is less than the width of the first and second end regions 20 and 22. The flexible strip of material 18 is preferably formed of an interwoven piece of fabric that allows the skin of the nose 12 to breathe to maximize comfort and minimize irritation. As an alternative, the strip of material 18 may be formed of a plastic film.

The tress member further includes resilient means 26 secured to a first side 28 of the strip of material 18. The resilient means 26 includes a first resilient band 30a secured by a first adhesive member 31a to the first side 28 of the strip of material 18. The first resilient band 30a is secured to the strip of material 18 adjacent a first edge 32 of the intermediate segment 24. In addition, a second resilient band 30b, spaced from the first resilient band 30a, is secured by a second adhesive member 31b to the first side 28 of the strip of material 18. The second resilient band 30b is secured to the strip of material 18 adjacent a second edge 36 of the intermediate segment 24. The first and second resilient bands 30a and 30b are oriented generally parallel to one another and substantially parallel to the longitudinal extent of the flexible strip of material 18. Each of the first and second adhesive members 31a and 31b is formed of an adhesive material such as double sided adhesive, foam tape.

Each of the first and second resilient bands 30a and 30b includes a plurality of grooves 38a and 38b, respectively, that extend substantially parallel to the respective resilient band 30a and 30b. As seen best in FIG. 2, the grooves 38a and 38b are formed in the exposed sides of the first and second resilient bands 30a and 30b (i.e., the sides of the first and second resilient bands 30a and 30b opposite that to which the first and second adhesive members 31a and 31b are secured). The grooves 38a and 38b create areas of reduced material to enhance the flexibility of the first and second resilient bands 30a and 30b in a direction perpendicular to the plurality of grooves 38a and 38b. In addition, each of the first and second resilient bands 30a and 30b includes first angled ends 40a and 40b, respectively, and second angled ends 42a and 42b, respectively. The first and second angled ends 40a,b and 42a,b extend towards the first side 28 of the strip of material 18 and help to prevent the first and second resilient bands 30a and 30b from readily separating from the strip of material 18 and the first and second adhesive members 31a and 31b when the truss member 10 is flexed. The first and second resilient bands 30a and 30b are formed of a plastic material.

As seen in FIG. 2, a second side 44 of the strip of material 18 includes a layer of an adhesive substance 46 that extends over the first and second end regions 20 and 22 and the intermediate segment 24. The adhesive substance 46 is biocompatible with the skin of the nose 12. A padded element 48 is secured to the median of the intermediate segment 24 via the adhesive substance 46. Readily removable, first and second release liners 49 and 50, respectively, cover the adhesive substance 46 on the first and second end regions 20 and 22, respectively, of the strip of material 18. The first and second release liners 49 and 50 cover the adhesive substance 46 and remain in place on the strip of material 18 until the nasal dilator 10 is to be used. The first and second release liners 49 and 50 also include extensions 51 and 52, respectively, that cover the padded element 48 and further act to protect the padded element 48 until the nasal dilator 10 is to be secured to the nose 12 of a wearer 14.

Figure 3:
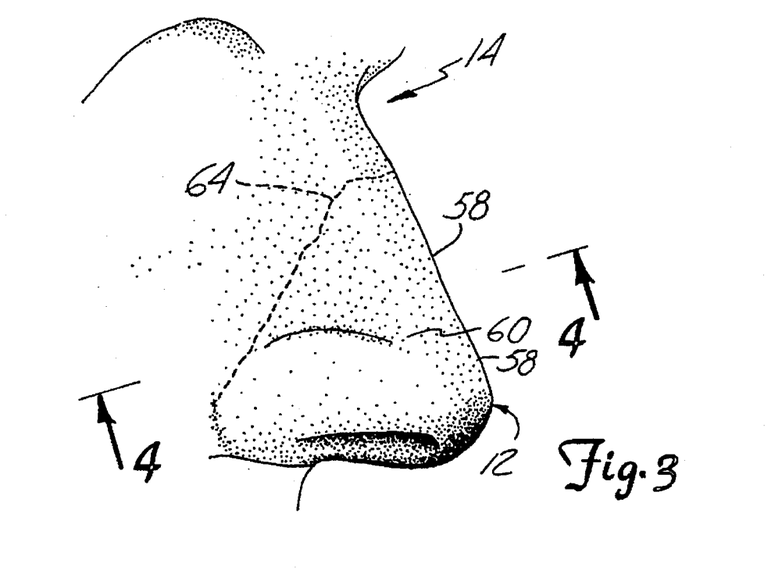
FIG. 3 is a perspective view similar to FIG. 1 with the nasal dilator in accordance with the present invention removed from the nose.
Figure 4:
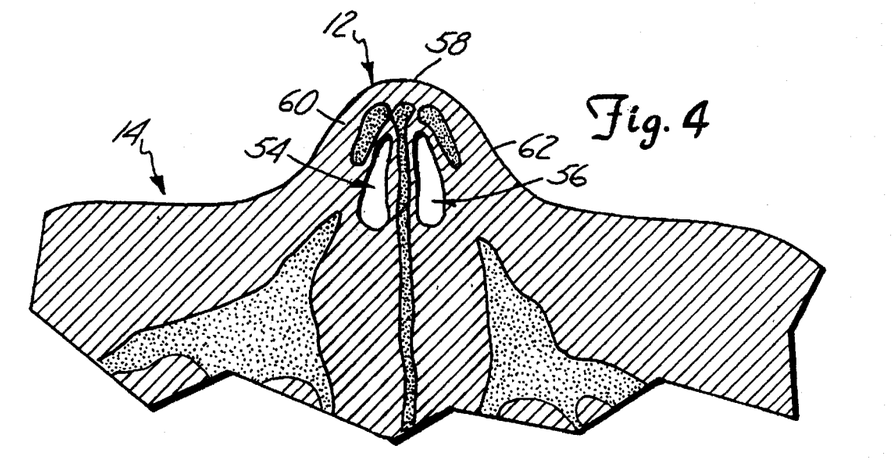
FIG. 4 is a sectional view taken along line 4—4 in FIG. 3 showing the nose in a state wherein no appreciable flow of air is occurring in the nasal passages.
Figure 5:
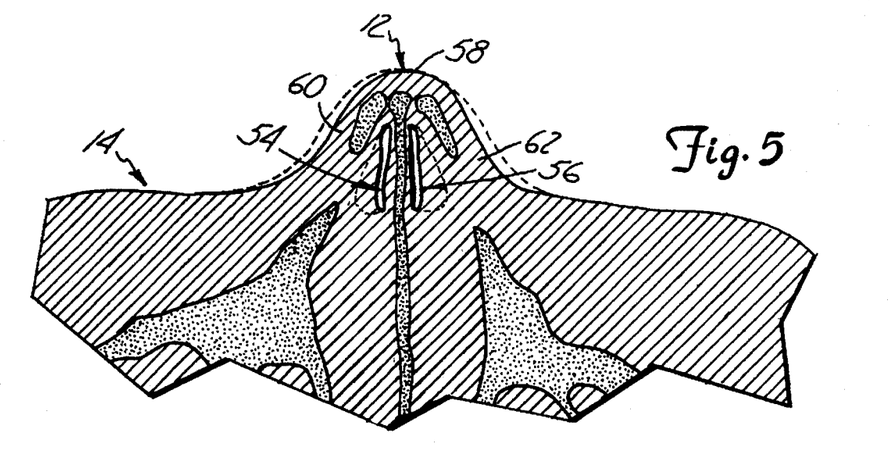
FIG. 5 is a sectional view similar to FIG. 4 showing the state of the nose during inhalation.

As seen in FIGS. 3 and 4, the nose 12 includes a first nasal passage 54, a second nasal passages 56 and a portion of the nose 12 known as the bridge 58 located between the first and second nasal passages 54 and 56. FIG. 4 shows the state of the first and second nasal passages 54 and 56 when no appreciable flow of air is occurring through the nasal passages 54 and 56. Due to a malformation, such as a deviated septum or swelling due to allergic reactions, outer wall tissue 60 and 62 of the first and second nasal passages 54 and 56, respectively, tends to be drawn in (i.e., collapse) during inhalation (see FIG. 5). This drawing in during inhalation is caused by reduced air pressure within the first and second nasal passages 54 and 56 as a result of an increase in air velocity as the in drawn breath travels through the first and second nasal passages 54 and 56. The portion (i.e., the ostium) of the outer wall tissue 60 and 62 drawn in during inhalation is that located between the nasal cartilage 64 (shown in dashed lines in FIGS. 1 and 3) and the entrance to the nasal passages 54 and 56. This drawing in of the outer wall tissue 60 and 62 causes nasal blockage. The nasal dilator 10 of the present invention remedies this problem.

Figure 6:
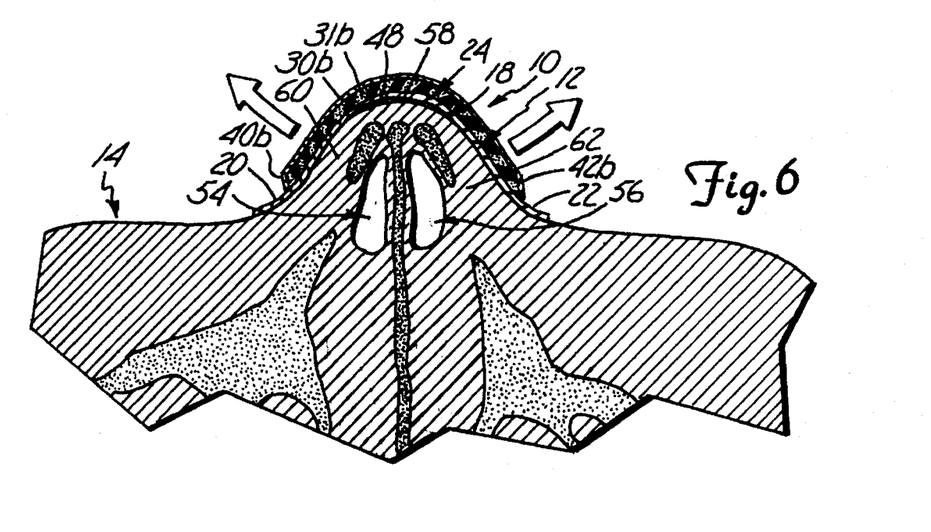
FIG. 6 is a sectional view taken along line 6—6 in FIG. 1 showing the state of the nose during inhalation with the nasal dilator in accordance with the present invention secured thereto.

To secure the nasal dilator 10 to the nose 12, the first and second release liners 49 and 50 are removed from the flexible strip of material 18 to expose the adhesive substance 46. As seen in FIGS. 1 and 6, the nasal dilator 10 is placed on the exterior of the nose 12 such that the intermediate segment 24 traverses the bridge 58 of the nose 12 and the first and second end regions 20 and 22 contact the outer wall tissue 60 and 62 of the first and second nasal passages 54 and 56. The adhesive substance 46 on the first and second end regions 20 and 22 releasably secures the truss member 16 to the outer wall tissue 60 and 62 of the first and second nasal passages 54 and 56. As seen in FIG. 6, the padded element 48 creates an absorbent adhesive void between the truss member 16 and the bridge 58. This absorbent adhesive void absorbs moisture due to perspiration or the like. With the nasal dilator 10 in place about the nose 12, the resiliency of the first and second resilient bands 30a and 30b (i.e., the tendency of the resilient bands to return to their normally planar state shown in FIG. 2) acts to stabilize the outer wall tissue 60 and 62 and thereby prevents the outer wall tissue 60 and 62 of the first and second nasal passages 54 and 56 from drawing in during breathing (i.e., during inhalation). In addition, the flexibility of the strip of material 18 and the first and second adhesive members 31a and 31b, the resiliency of the first and second bands 30a and 30b, and the flexibility of the first and second bands 30a and 30b due to the grooves 38a and 38b, all allow the nasal dilator 10 to closely conform to the curves of the nose of each individual wearer.

This nasal dilator 10 is of efficient design and effectively prevents the outer wall tissue 60 and 62 of the first and second nasal passages 54 and 56 of the nose 12 from drawing in during breathing. In addition, the nasal dilator 10 provides effective relief of nasal blockage during inhalation without the irritation and discomfort normally associated with nasal dilators that are inserted within the nasal passages. Moreover, this nasal dilator 10 can be worn at night when the inhalation nasal blockage problem is most acute, without the anxiety and inconvenience normally associated with custom made, internally worn nasal dilators.

The adhesive void at bridge 58 of nose 12 of user 14 formed by the use of padded element 48 to cover a portion of adhesive 46 can, for some users, cause irritation. Such irritation is thought to arise from relative movements between padded element 48 and the skin at bridge 58 of nose 12, movements which come about because of facial muscles causing movement of that skin or because of external objects, such as a pillow, applying forces to dilator 10 at various times during use. This problem can be avoided, of course, by not using pad element 48 so that adhesive 46 adheres to all of bridge 58 and outer wall tissues 60 and 62 of nose 12. Such an omission of pad element 48, on the other hand, eliminates the benefits derived from its use such as the avoidance of peel forces on the skin of bridge 58 during removal of dilator 10 after use.

An alternative which results in providing some of the benefits of both a fully adhesive dilator and a dilator with an intermediate adhesive void can be provided by forming a dilator having a partial adhesive void at the intermediate location between the ends thereof. Such a partial adhesive void can be provided through having the adhesive present being effective in adhering to the skin of the bridge of the user's nose only over some fraction of the intermediate surface area between the end surfaces of the dilator. In that intermediate segment that goes over bridge 58 of nose 12 of user 14, a typical choice of effective adhesion area would be 40 to 50% of the entire dilator intermediate surface area for a biocompatible adhesive material typically used for adhesive substance 46. The extent of the reduction in adhesion at the skin of bridge 58 and nose 12 by a partial adhesive void can be conveniently and consistently determined by the choice of the fraction of the intermediate area in which the adhesive is effective, a choice which can be made and maintained in the manufacturing process for dilator 10.

The fractional reduction of the effective adhesive area from the total intermediate surface area covering bridge 58 of nose 12 during use permits sufficient adhesion to avoid most of the irritation occurring due to relative motion of the skin on bridge 58 and dilator 10, but yet provides reduced peel forces during removal of dilator 10 from nose 12 of user 14 after completion of the use thereof. In such an arrangement, there will be no reduction in the adhesion force which occurs between the ends of dilator 10 and wall tissues 60 and 62 of nose 12. As a result, the outward spring force of dilator 10 will be balanced by the reactive force of wall tissues 60 and 62 without separation of the ends of dilator 10 from those tissues to thereby maintain wider nasal passages adjacent such wall tissues.

Figure 7:
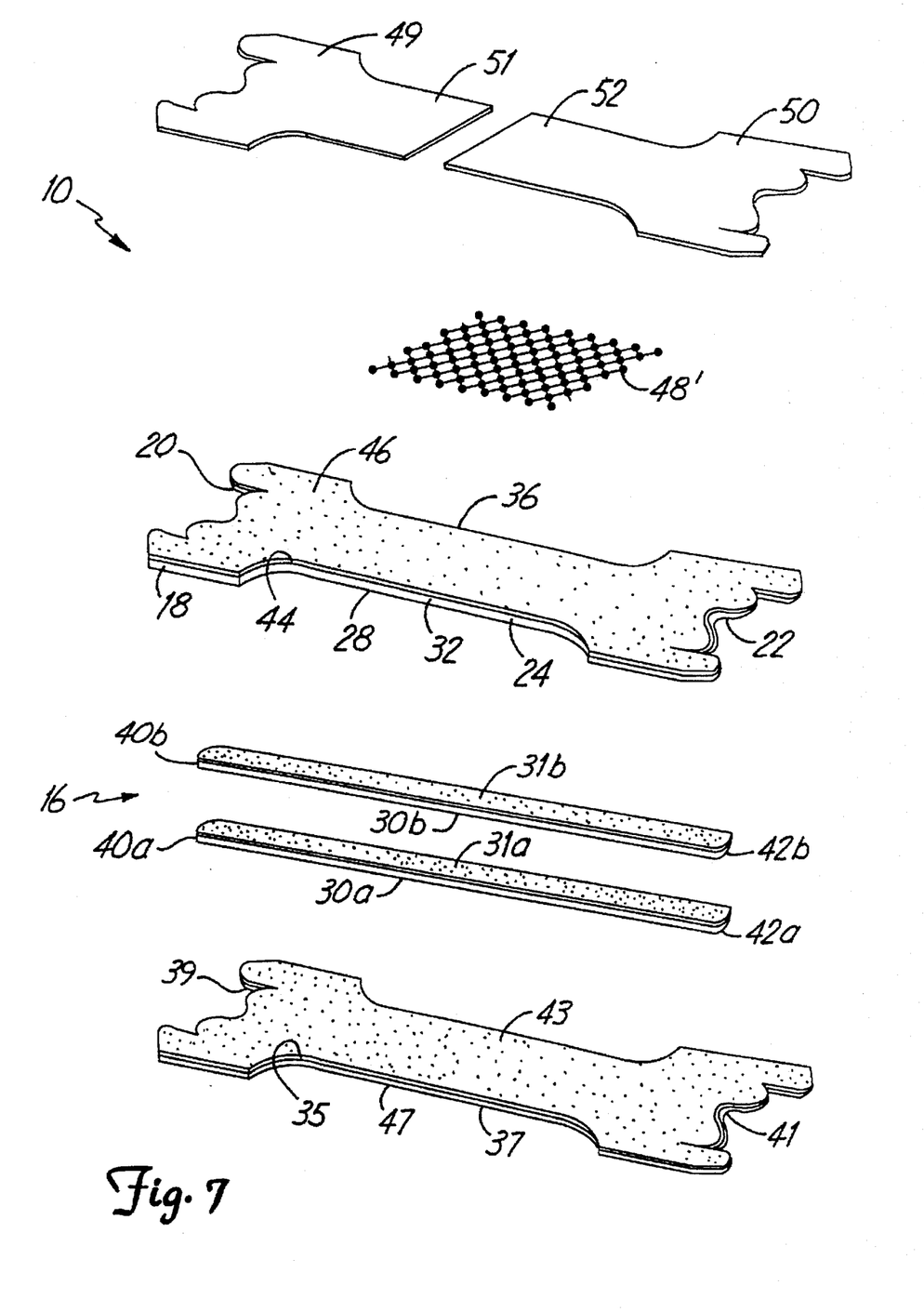
FIG. 7 is an exploded perspective view showing the components of an alternative dilator in accordance with the present invention.

A dilator 10 having a structure providing a partial adhesive void in an intermediate location between the end surfaces thereof is shown in the exploded prospective view of that dilator provided in FIG. 7. Dilator 10 comprises unitary, or single body, truss member 16 which includes flexible strip of material 18 having first and second end regions 20 and 22 coupled together by intermediate segment 24 as before. First and second end regions 20 and 22 are each shown with a scalloped end shape provided between a pair of side extensions extending further outward along the length of dilator 10, an arrangement provided to reduce unintended peeling of dilator 10 from the user's nose 12 during use.

Again in truss member 16 are first and second resilient bands 30A and 30B, as before, and formed of industrial grade, biaxial oriented polyester about 0.010 inches thick and typically from 0.080 to 0.135 in. wide. These resilient bands are again secured to side 28 of flexible material strip 18 by strips of acrylic, pressure sensitive, biocompatible adhesive material 31A and 31B, but these strips are shown in FIG. 7 as homogeneous adhesive material layers coated onto these resilient bands rather than being shown separately as in FIG. 2. The ends of resilient bands 30A and 30B are designated 40a, 40b, 42a and 42b as before but are not angled in this version. The grooves used in the resilient bands in the dilator of FIG. 2 are omitted in the more torsionally flexible bands of the dilator of FIG. 7.

The side of flexible material strip 18 opposite its side 28 to which resilient bands 30A and 30B are secured, side 44, has again adhesive substance layer 46 extended thereover to cover end regions 20 and 22 and intermediate segment 24 with this substance again being a porous, acrylic, pressure sensitive, biocompatible adhesive. However, rather than providing padded element 48 on adhesive substance 46 at intermediate segment 24 as in FIG. 2, a netting or mesh layer, 48', is instead secured to adhesive substance 46 at the location of intermediate segment 24.

Netting 48' is a polyethylene material netting having a thickness of around 0.004 in. This netting has significant mechanical strength even when wet, and allows moisture to easily wick therealong so that it may be transmitted away from the skin on bridge 58 of user's nose 12 through the vapor porous materials thereover. The netting material should not introduce any contaminants and should be of an odorless nature. In its mechanical characteristics, the material should be as soft as, or softer than, flexible material strip 18 (a material which can be a non-woven, spun lace, 100% polyester fabric such as is available from E. I. DuPont Nemours & Co. under the trademark SONTARA®), that is, the material should drape over uneven surfaces under the influence of gravity in a manner so as to follow those surfaces as well as does flexible material strip 18. This characteristic indicates that the netting material can also compress in on itself sufficiently to prevent significant puckering of that material when forced about a curved surface over bridge 58 of user's nose 12 even though that material is fabricated in a substantially planar state. A suitable material for netting 48' is offered under the trademark DELNET® by Applied Extrusion Technologies, Inc. of Middletown, Del.

Netting 48' thus serves as both a partial mask in covering portions of adhesive 46 at the location of intermediate segment 24, and as a spacer between the skin of bridge 58 of user's nose 12, when in use, and portions of both adhesive material 46 and flexible material strip 18. By both covering portions of adhesive material 46 in its masking function, and by reducing the compression of adhesive 46 against the skin of bridge 58 of user's nose 12, a reduced adhesion is obtained between the skin of bridge 58 and the portion of dilator 10 at its intermediate segment 24. The adhesion obtained is sufficient to prevent relative movement of dilator 10 with respect to the skin of bridge 58 of user's nose 12 in most situations, but is sufficiently reduced to allow removal of dilator 10 after completion of use without experiencing the peel forces between dilator 10 and that skin which would otherwise occur in the absence of netting material 48'.

Unitary truss member 16 further includes a flexible strip of top, or outer, porous non-woven material, 37, with first end region 39 and second end region 41 along with intermediate segment 47. These end regions and intermediate segment of top material 37 have the same size and shape as end regions 20 and 22 of flexible material strip 18 and intermediate segment 24 thereof. A water vapor porous, acrylic, pressure sensitive, biocompatible adhesive material layer, 43, is provided on surface 35 of top material 37 to secure top material 37 to resilient bands 30A and 30B and to the exposed portions of flexible material strip 18 not covered by these resilient bands in their being secured thereto. Top material strip 37 aids in preventing the resilient bands from separating from base material 18 when dilator 10 is flexed around nose 12 in use, and aids in maintaining the integrity of base material 18 during removal of dilator 10 from the user's nose after use.

Again, first and second release liners 49 and 50 cover the exposed portions of adhesive substance layer 46 over first and second end regions 20 and 22 of flexible strip of material 18. Release liners 49 and 50 are provided to cover adhesive 46 until dilator 10 is ready to be used at which time they are peeled off by the user to expose adhesive substance 46. First and second release liners 49 and 50 again include extensions 51 and 52 to cover netting 48' to shield that element and the portions of adhesive 46 exposed there from the external world until dilator 10 is to be used.

Figure 8:
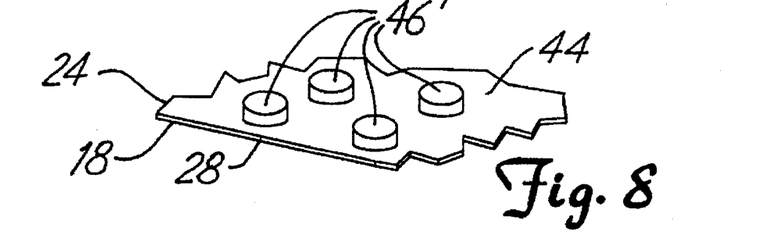
FIG. 8 is a fragmentary view of an alternative for a portion of the dilator shown in FIG. 7.

Other arrangements can be used to provide the partial adhesive void structure desired at intermediate segment 24 rather than the use of netting material 48' at that location as shown in FIG. 7. One such alternative is shown in the fragmentary view of FIG. 8 of a portion of an alternate construction for intermediate segment 24 of dilator 10. There, adhesive substance 46, rather than being masked by netting material 48' is shown partially removed by etching or dissolving through mask portions thereof to leave a plurality of separated adhesive regions, 46'. Alternatively, rather than outright removal, the portions of adhesive 46 not to be effective in adhering dilator 10 to the skin of bridge 58 could be chemically deactivated to no longer adhere in the deactivated regions. The amount of adhesion reduction from the adhesion provided by the use of adhesive layer 46 without modification is controlled by the size of effective adhesive regions 46' and by the separation provided between these regions. In a further alternative, separated adhesive regions 46' could instead be additively provided rather than substractively provided such as in the form of separated parallel rows of adhesive material (or separated adhesive spots as in FIG. 8) specifically deposited on flexible material strip 18 in this form to provide the desired partial adhesive void.

Figure 9:
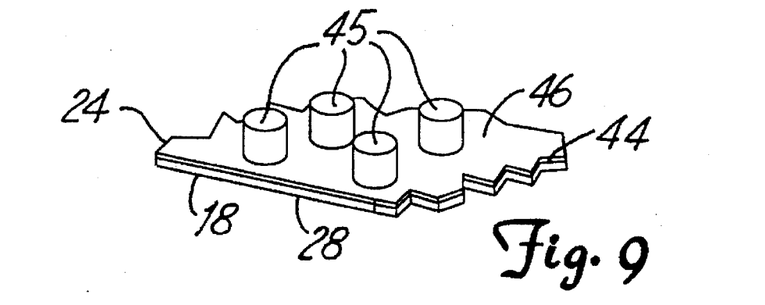
FIG. 9 is a fragmentary view of another alternative for a portion of the dilator shown in FIG. 7.

Such treatments or depositions of adhesive material 46 and intermediate segment 24 of dilator 10 may prove relatively expensive when compared with methods involving partially covering a full layer of adhesive substance 46 at intermediate segment 24 such as occurs with use of netting 48'. FIG. 9 shows an alternative method for covering portions of adhesive substance 46 in the fragmentary view provided there of a portion of intermediate segment 24 using the construction for this alternative. There, a plurality of spaced-apart polyethylene disks or beads, 45, are shown adhered to adhesive layer 46 to again cover portions of that adhesive layer, and to space portions of that adhesive layer and flexible material strip 18 at intermediate segment 24 apart from the skin of bridge 58 of user's nose 12. Such polyethylene disks may, for instance, be 0.015 inches in diameter and 0.005 inches thick. These polyethylene disks can be provided on adhesive layer 46' through the use of a transfer drum, and again the size of the disks and their separation control the amount of adhesion reduction obtained.

Figure 10:
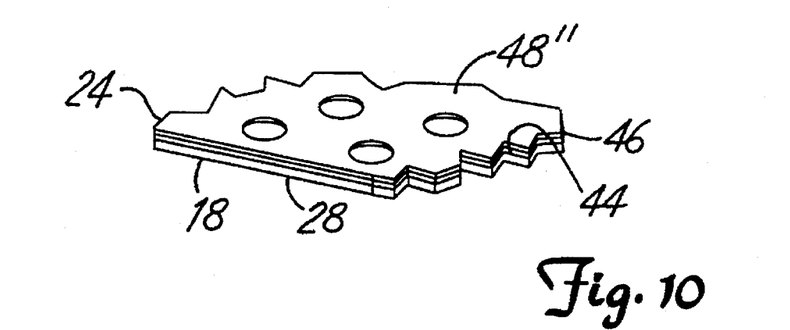
FIG. 10 is a fragmentary view of a further alternative for a portion of the dilator shown in FIG. 7.

Alternatively, adhesive material 46 at intermediate segment 24 can be covered by a perforated layer having the perforations controlled in size and in separation from one another to control the reduction of adhesion resulting from the use thereof on adhesive layer 46. One possibility is the use of a perforated polyethylene sheet, 48", of 0.0005 to 0.0015 inches thickness to be positioned an adhesive layer 46 at intermediate segment 24 as shown in the fragmentary view of FIG. 10 of that segment illustrating such an alternative. Another possibility would be to apply a biocompatible varnish with suitable spaced openings therein over adhesive material layer 46.

Figure 11:
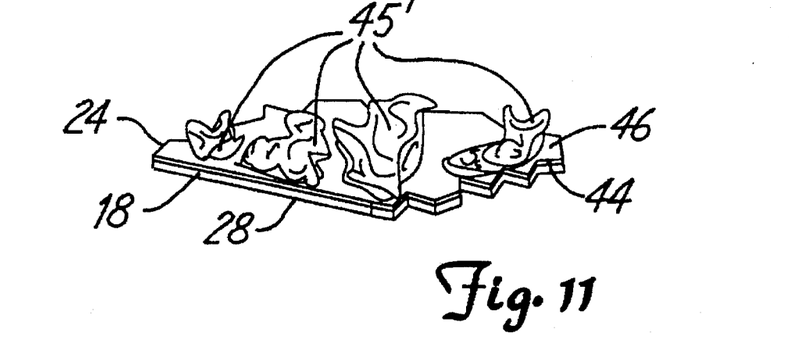
FIG. 11 is a fragmentary view of yet another alternative for a portion of the dilator shown in FIG. 7.

Finally, the fragmentary view in FIG. 11 of intermediate segment 24 shows a further alternative in which a fine polyethylene powder, 45', is used to cover more or less randomly positioned portions of adhesive layer 46. Here, the fineness of the polyethylene powder grains and the density by which they are applied to provide the desired average area of exposed adhesive 46 controls the resulting adhesion reduction obtained.

Although the present invention has been described with reference to preferred embodiments, workers skilled in the art will recognize that changes may be made in form and detail without departing from the spirit and scope of the invention.

What is claimed is:

1. A dilator capable of introducing separating stresses in outer wall tissues of a section of human anatomy, comprising:

a truss of a single body having a pair of spaced-apart end surfaces which, if forced toward one another from initial positions to substantially reduce direct spacing therebetween by a spacing reduction force external to said tress, results in restoring forces in said truss tending to restore said direct spacing between said end surfaces;

ends engagement means adhered to said end surfaces and capable of engaging exposed surfaces of such outer wall tissues sufficiently to remain so engaged against said restoring forces; and an intermediate engagement means adhered to said truss at a surface thereof located between said end surfaces and capable of engaging exposed surfaces of human anatomy between the exposed surfaces of the outer wall tissues engaged by said ends engagement means but with less adhesion than that exhibited by said ends engagement means in engaging the outer wall tissues.

2. The dilator of claim 1 wherein said intermediate engagement means is formed of an adhesive adhered to said truss and covered by a layer of material having openings extending therethrough.

3. The dilator of claim 2 wherein said layer is a polymer sheet.

4. The dilator of claim 2 wherein said layer is a polymer netting.

5. The dilator of claim 1 wherein said intermediate engagement means is formed of an adhesive adhered to said truss and covered with a film having openings extending therethrough.

6. The dilator of claim 5 wherein said film is a residue of a material deposition including a liquid.

7. The dilator of claim 1 wherein said intermediate engagement means is formed of an adhesive adhered to said tress and covered with a plurality of separated regions each containing a non-adhesive material.

8. The dilator of claim 7 wherein said non-adhesive material is a polymer material.

9. The dilator of claim 1 wherein said intermediate engagement means is formed of a plurality of separated regions each containing an adhesive adhered to said tress.

* * * * *

UNITED STATES PATENT AND TRADEMARK OFFICE
CERTIFICATE OF CORRECTION

PATENT NO. : 5,653,224
DATED : AUGUST 5, 1997
INVENTOR(S) : BRUCE C. JOHNSON

It is certified that error appears in the above-indentified patent and that said Letters Patent is hereby corrected as shown below:

Col. 1, line 65, delete "dram", insert --drawn--

Col. 2, line 41, delete "tress", insert --truss--

Col. 2, line 53, delete "tress", insert --truss--

Col. 2, line 66, delete "oft he", insert --of the--

Col. 3, line 26, delete "tress", insert --truss--

Col. 4, line 23, delete "tress", insert --truss--

Col. 7, line 36, delete "mariner", insert --manner--

Col. 9, line 31, delete "tress", insert --truss--

Col. 10, line 27, delete "tress", insert --truss--

Col. 10, line 33, delete "tress", insert --truss--

Signed and Sealed this

Thirteenth Day of January, 1998

Attest:

BRUCE LEHMAN

Attesting Officer     Commissioner of Patents and Trademarks